(12) United States Patent
Husemann et al.

(10) Patent No.: US 11,827,874 B2
(45) Date of Patent: Nov. 28, 2023

(54) BIOREACTOR SYSTEM AND METHOD

(71) Applicant: Sartorius Stedim Biotech GmbH, Goettingen (DE)

(72) Inventors: Bernward Husemann, Goettingen (DE); Simon Topp-Manske, Lohfelden (DE); Bjoern Nickel, Hessisch-Lichtenau (DE); Marco Leupold, Kassel (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 333 days.

(21) Appl. No.: 17/156,701

(22) Filed: Jan. 25, 2021

(65) Prior Publication Data

US 2021/0139835 A1     May 13, 2021

Related U.S. Application Data

(62) Division of application No. 15/577,574, filed as application No. PCT/EP2016/000406 on Mar. 8, 2016, now Pat. No. 10,947,489.

(30) Foreign Application Priority Data

Jun. 2, 2015    (DE) .................... 10 2015 007 060.6

(51) Int. Cl.
*C12M 1/00* (2006.01)
*C12M 3/00* (2006.01)
*C12M 1/34* (2006.01)
*C12M 1/06* (2006.01)

(52) U.S. Cl.
CPC ............ *C12M 29/26* (2013.01); *C12M 23/14* (2013.01); *C12M 23/22* (2013.01); *C12M 23/26* (2013.01); *C12M 23/28* (2013.01); *C12M 23/38* (2013.01); *C12M 23/48* (2013.01); *C12M 27/02* (2013.01); *C12M 41/00* (2013.01); *C12M 41/12* (2013.01)

(58) Field of Classification Search
None
See application file for complete search history.

(56) References Cited

U.S. PATENT DOCUMENTS

| | | | | |
|---|---|---|---|---|
| 4,041,640 | A | * 8/1977 | Itanami | .................. C12M 21/02 366/261 |
| 4,653,388 | A | * 3/1987 | Wilkinson | ................ C12C 7/22 426/16 |
| 6,673,598 | B1 | 1/2004 | Akers et al. | |
| 2003/0226857 | A1 | 12/2003 | Bibbo et al. | |

(Continued)

FOREIGN PATENT DOCUMENTS

WO     2015-039034     3/2015

OTHER PUBLICATIONS

International Search Report dated Aug. 16, 2016.

*Primary Examiner* — Holly Kipouros
(74) *Attorney, Agent, or Firm* — Gerald E. Hespos; Michael J. Porco (57) ABSTRACT

A bioreactor (1; 2; 3) includes a receiving container (10) for receiving a disposable bag (44). A bottom surface (11) of the receiving container (10) is designed to support the disposable bag (44) in the receiving container (10). An outlet opening (5) is formed in the bottom surface (11) and tapers down with respect to the ground for receiving a drain port (45) of the disposable bag (44). The drain port is complementary to the outlet opening (5).

13 Claims, 7 Drawing Sheets

(56) References Cited

U.S. PATENT DOCUMENTS

| | | | |
|---|---|---|---|
| 2006/0246581 A1* | 11/2006 | Tomita | C12M 23/14 435/243 |
| 2008/0139865 A1* | 6/2008 | Galliher | C12M 41/14 588/249 |
| 2009/0290962 A1* | 11/2009 | Fisher | C12M 23/14 414/816 |
| 2010/0112700 A1 | 5/2010 | Shaaltiel et al. | |
| 2011/0200954 A1* | 8/2011 | Sassow | C12M 23/36 431/2 |
| 2011/0310696 A1 | 12/2011 | Goodwin et al. | |
| 2012/0175012 A1* | 7/2012 | Goodwin | B01F 23/23124 141/11 |
| 2013/0039810 A1* | 2/2013 | Riechers | C12M 41/02 422/82.05 |
| 2013/0081995 A1 | 4/2013 | Larsen et al. | |
| 2013/0101982 A1 | 4/2013 | Goodwin et al. | |
| 2015/0056694 A1 | 2/2015 | Akerstrom | |

\* cited by examiner

FIG. 8B

BIOREACTOR SYSTEM AND METHOD

CROSS REFERENCE TO RELATED APPLICATION

This application is a divisional of U.S. patent application Ser. No. 15/577,574, filed Mar. 12, 2018.

BACKGROUND

Field of the Invention

The present invention refers to bioreactor systems for receiving a disposable bag and to a method for receiving a disposable bag in a bioreactor system.

Related Art

Bioreactor systems, also called bioreactors, and pallet tanks are used as devices for receiving and storing biological mediums, such as fluids. Biological mediums may be provided in disposable bags, which may comprise a volume of several hundred liters. Biological mediums are introduced into a disposable bag in the bioreactor, in which they are temperature regulated in a predetermined time interval usually of several hours to a predetermined temperature. In such a bioreactor, various tests on the biological medium may be performed.

The handling of a bioreactor is usually performed within a sterile environment, so that the bioreactor has to fulfill particularly stringent requirements regarding quality assurance. Moreover, handling of the sometimes-heavy disposable bags as well as the control of the bioreactors are onerous and complex.

The object of the invention is to improve control and/or handling of a bioreactor system of above said type.

SUMMARY

A first aspect refers to a bioreactor system for receiving a disposable bag comprising a receiving container for receiving the disposable bag, wherein a bottom surface of the receiving container is adapted to support the disposable bag in the receiving container. An outlet opening, which is tapered downward relative to Earth's frame of reference, is formed in the bottom surface for receiving a drain port of the disposable bag, the drain port being complementary to the outlet opening.

The bioreactor system may be a bioreactor, a pallet tank and/or a stirring vessel reactor of above said type, which may be adapted for receiving disposable bags having a volume of 1 liter up to about 2000 liters, in particular a volume between 200 liters and 1000 liters. The system may in particular be adapted for receiving disposable bags, in which a biological medium such as a fluid is disposed, which is stored, temperature-regulated and/or has otherwise to be tested in the system during a predetermined time span.

The receiving container of the system provides a container inner space, which is adapted for receiving the disposable bag. The receiving container may be adapted for receiving a predetermined type of disposable bag, such as a disposable bag of a particular manufacturer and/or having a predetermined filling volume. In particular, the receiving container is adapted for receiving a disposable bag with a draining port having a predeterminable form. The container walls of the receiving container define the container inner space. The container walls of the receiving container do not necessarily completely surround and/or delimit the container inner space. The receiving container may be provided, for example, on its upper edge, with a stirring opening, through which a stirring device may be connected to the disposable bag in the container inner space. The stirring device may be provided as a drive, which may be connected to a stirring rod, which is disposed within the disposable bag. Such a stirring device is preferably provided at the upper end of the receiving container. The receiving container may thus be in particular provided without a lid and/or with an open top.

The terms "up", "down", "lateral", "vertical", "horizontal", "height", etc., refer, in the context of the present invention, to the Earth's frame of reference, in which the bioreactor system is positioned in an operating position.

The disposable bag is preferably placed in the receiving container in such a way that it rests on a bottom of the receiving container and is in direct physical contact with the container walls of the receiving container, in particular in contact with the bottom surface of the receiving container and possibly with the container walls adjacent to the bottom surface. While the biological medium in the receiving container is examined, the disposable bag is supported by the bottom surface.

After or during the examination of the biological medium, the medium can be at least partially discharged out of the receiving container. In order to avoid having to lift the very heavy disposable bag from the storage container, the contents of the disposable bag are emptied, while the disposable bag is still positioned in the receiving container. To this purpose, in the bottom surface of the receiving container, the outlet opening is formed, through which the biological medium may be selectively discharged. The bottom surface can be funnel-shaped towards the outlet opening, whereby the disposable bag can be emptied almost completely.

The bioreactor system is adapted to receive disposable bags with a drain port which tapers outwardly, i.e. away from the interior of the bag. The drain port is formed in the bottom of the disposable bag and protrudes at least partially from the disposable bag, downwards when in the operating position. The drain port is not only formed in the shape of a straight cylinder or simple tube, but has at least partially external dimensions, which taper in a direction away from the bag. The outlet opening in the bottom surface is exactly complementarily shaped with respect to this special outwardly (in operating position: downwardly) tapering drain port and vice versa.

If a disposable bag having such a complementary drain port is introduced into the bioreactor system, then the drain port essentially slides of its own accord and/or automatically into the downwards tapering outlet opening. To this end, the bottom surface of the receiving container may be completely or at least partially provided with a slope down towards the outlet opening, in order to assist and/or facilitate the sliding in of the complementary drain port into the outlet opening. The downward tapering outer dimensions of the drain port and/or the downward tapering inner surfaces of the outlet opening thus provide sliding surfaces for aligning and arranging the drain port. Moreover, the drain port of the disposable bag may be led to the outlet opening in its target position while being introduced into the receiving container at the end of a tube laid through outlet opening.

On the drain port of the disposable bag, additional tubes and/or locks of sterile connectors may be formed and provided, which may also be inserted through the bottom surface. The sterile connectors themselves may be larger than the drain port. The outlet opening of the bottom surface is provided as a passage, which allows both receiving the drain port of the disposable bag and the passing through of at least one tube and/or lock of a sterile connector. The outlet opening receives the drain port, without letting it fall completely through the outlet opening. The smallest inner diameter of the outlet opening is thus smaller than the largest outer diameter of the complementary drain port.

Due to the predetermined outer shape of the drain port, the outlet port may be adjusted exactly to the outer shape of the complementary drain port independently of the size of the optional additional sterile connectors. In the outlet opening of the complementary drain port, only the complementary drain port is supported, wherein optionally one (or more) additional tube(s) for the sterile connectors are passed through. The one (or more) optional sterile connector(s) may be mounted below the outlet opening at the end of the tube (s). Thus, also sterile connectors can be used which are larger than the outlet opening.

In the operating position of the bioreactor system, the complementary drain port of the disposable bag is firmly supported and/or held in the downwards tapering outlet opening. The drain port self-aligns into the target position due to the matching form surfaces of the drain port and the outlet opening. This also applies to the position of a stirring shaft optionally centered on the drain port, for stirring the inner space of the disposable bag. This allows for a secure and low friction operation of the stirring shaft. In order to output the biological medium, the drain port may be opened, for example while it is supported in the outlet opening.

This safe and efficient support of the drain port in the outlet opening improves handling of the bioreactor system, in particular when the unwieldy disposable bag is positioned in the receiving container and when outputting the biological medium. In particular, the disposable bag is hardly accessible at the bottom of the receiving container. The simplified alignment considerably simplifies the handling, and in particular the aligning, in the receiving container.

In an embodiment, the outlet opening is at least partially downwardly tapered, having an essentially conical and/or semispherical and/or semi-ellipsoidal shape. The shape of the cone, a hemisphere a semi-ellipsoid or, for example, a combination of a cylinder and one of these shapes is particularly suitable for a complementary drain port, which slides automatically and/or in a guided way into the complementarily tapering outlet opening.

In an embodiment, the bioreactor system has a fixing element for fixing the complementary drain port of disposable bag in the outlet opening. Thus, a locking of the outlet opening is provided. The fixing element may be a mechanical fixing element such as a fixing bolt, which may engage into a complementary engaging element (such as a groove) in the drain port. The fixing element allows fixing the drain port in the operating position, thus improving and stabilizing the alignment and positioning of the entire disposable bag in the receiving container, in particular while stirring the biological medium.

The locking and/or the fixing element may be screwed, welded and/or glued to the bottom surface.

The bioreactor system may also be provided with a sensor for detecting the opened state of the lock of the outlet opening.

In an elaboration, the bioreactor system has a remote control for opening and/or closing the fixing element. The remote control may be an electrical remote control or a mechanical remote control. By means of the remote control, the lock of the outlet opening may be easily actuated, in particular without requiring observation of the possibly inaccessible outlet opening. At the position of the remote control, the opened state of the lock may be recognized without looking at the lock. The fixing element easily engages by means of the remote control, without a direct actuation of the fixing element. Thus the space requirements for locking on the bottom surface are reduced.

A mechanical remote control may be provided with at least one operating rod, which extends to the outlet opening and by which the fixing element may be closed and/or opened. The operating rod may be mechanically coupled to a closing ring, which surrounds the outlet opening and the rotation of which by means of the operating rod controls the position of the fixing element. The operating rod may have a length of at least one meter, so that the fixing element is easily operated. Alternatively, the remote control may be implemented by a Bowden cable, a servomotor, a rod, pneumatically and/or hydraulically.

In an embodiment, the drain port, which is complementary to the outlet opening, is a separate component of the bioreactor system, which may be secured to a standard drain port integrated in the disposable bag, in such a way that the complementary drain port tapers in a direction away from the inner space of the disposable bag. The complementary drain port is secured to the standard drain port before introducing the disposable bag into the receiving container. The standard drain port usually has a tubular shape. The complementary drain port is placed around this standard drain port and/or is secured to the same. Thus any disposable bag may be aligned to the outlet opening of the bioreactor, wherein by means of the complementary drain port the disposable bag may be converted into a disposable bag having a downwards tapering drain port, which is complementarily shaped with respect to the outlet opening. The complementary drain port may be a disposable component or a reusable component and is part of the bioreactor system.

In an elaboration of this embodiment, the complementary drain port is a multipart component. The drain port may in particular be made of two parts having two half-shells, which may be placed around the standard drain port. The single parts forming the drain port may be aligned and/or fixed to each other by respective fixing elements integrated into the individual parts. These fixing elements may have magnets, a snap lock, a latch lock and/or alignment pins with complementary alignment openings.

A second aspect refers to a bioreactor system for receiving a disposable bag, having a receiving container for receiving the disposable bag and one working platform which is essentially adjacent to an outer wall of the receiving container. The surface of the working platform, on which the operator may walk, is positioned about 80 cm to about 140 cm below an upper edge of the receiving container.

The bioreactor system may be a bioreactor of above said type. The bioreactor system according to the second aspect is similar to the bioreactor system of the first aspect, so that many or even all information regarding the bioreactor system of the first aspect may also be referred to the bioreactor system of the second aspect and vice versa.

In the bioreactor system of the second aspect a working platform is provided, on which a standing operator may comfortably access the upper edge and thus the stirring opening at the top end of the receiving container. Further auxiliary devices such as a filter, at least one sensor, at least a probe, at least one motor and/or similar devices may be disposed on the stirring opening, which devices may be operated by the operator from the working platform. Moreover, conduits for additional mediums to be fed may be provided on the upper edge, wherein the feeding may be easily monitored and/or controlled from the working platform.

The working platform is provided above the ground, on which the bioreactor system is positioned in the operating position. The working platform is essentially a walkable surface, which is adapted for at least one person or preferably at least two persons walking on the same, thus supporting a load of at least 80 kg or at least 160 kg. The surface is in particular essentially horizontal.

The working platform is adjacent to an outer surface of the receiving container and thus can extend completely on the receiving container. Thus, also the operator can reach the receiving container, so that an efficient and easy operation of the auxiliary devices and/or of the stirring device on the upper edge of the receiving container is obtained.

The surface of the working platform is positioned about 80 cm to about 140 cm below the upper edge of the receiving container, preferably between about 80 cm and about 120 cm, particularly preferred between about 95 cm and about 110 cm below the upper edge of the receiving container. With this configuration, the upper edge of the receiving container may easily be reached by operators having different body sizes. The distance is also provided in a way that the center of mass of most people lies below the upper edge, so that an accidental falling of the operator into the receiving container can be avoided.

The working platform is preferably positioned only on an outer surface of the receiving container, such as only on the rear or front side of the bioreactor system, for example, without surrounding the receiving container. This allows saving space and is sufficient for operation.

Due to the working platform, on one hand, the use of an additional ladder for operating the bioreactor is superfluous, and on the other hand, the operator on the working platform may reach up to the receiving container, while securely standing on the working platform. Thus the operation of the bioreactor is considerably improved and simplified.

The bioreactor system according to the second aspect may have all additional characteristics of the bioreactor system of the first aspect and vice versa.

In an embodiment of the bioreactor system having the working platform, the bioreactor system has an integrated ladder, which leads from the ground, on which the bioreactor system rests in the operating position, up to the walkable surface of the working platform. The ladder simplifies the walking on the working platform and allows the omission of a separate ladder for climbing up to the working platform. The ladder may have the form of a plurality of rungs, which are integrated into the bioreactor system.

In an embodiment of the bioreactor system with the working platform, the working platform has a railing, which at least partially surrounds the working platform. The railing secures an operator on the working platform in at least one direction, for example in the direction away from the receiving container. A railing is provided in particular for working surfaces, which are more than 65 cm above the ground. Thus, the operation of the bioreactor system is safer.

In an alternative embodiment of the bioreactor system with the working platform, the surface of the working platform is positioned at a maximum height above ground of 65 cm, wherein the working platform lacks a railing. On a lower working platform a railing may be omitted, without limiting safety. Thus the freedom of movement and thus the operating comfort are increased.

In embodiment of the bioreactor system with the working platform, the working platform is at least partially extractable and/or foldable in an open position. This is particularly advantageous in the case of limited spaces, since the bioreactor system may be very compact and easier to transport.

An embodiment refers to a bioreactor system having a receiving container for receiving a disposable bag, in which a collecting tray for collecting a fluid exiting the receiving container is positioned below the receiving container. Usually, no medium should exit the receiving container in an uncontrolled way. In case of a defect or leak in the disposable bag and/or in the receiving container, as well as in case of a defect or leak in the temperature regulating circuit, the collecting tray may collect the exiting liquid, before it flows on the ground. Thus the danger of contaminating the ground is reduced and the disposal of the exited liquid is simplified.

In an elaboration, the collecting tray has a cladding made of plastic, and/or its position below the receiving container may be exactly adjusted. In particular, the height of the collecting tray above the ground may be set, for example for compensating an uneven ground. The cladding of the tray may either be a fixedly integrated plastic coating and/or an insertable disposable bag.

According to one embodiment, the bioreactor system has at least one system rail for attaching at least one auxiliary device. The system rail is used for securing an auxiliary device such as a probe or for securing cables or other feeding lines. With the system rail, the bioreactor system can be individually tailored to specific applications. The system rail can be standardized and/or be formed to be at least 10 cm long.

Herein, the bioreactor system may include a window such as an observation and/or probing window in the receiving container, adjacent to which the system rail is disposed. The window is transparent and is used for observation and/or monitoring of the biological medium in the bioreactor. In case of elongated windows, the system rail may be arranged substantially in parallel to the longitudinal axis of the window. In particular, adjacent to all windows, at least one system rail may be formed on an outer wall of the receiving container.

In an elaboration, the system rail is positioned at a distance of about 3 cm to about 20 cm from the window. The distance data are the smallest distance between a part of the system rail and a part of the window. The system rail may preferably be positioned at the nearest possible position to the window, in order to position an auxiliary device as near as possible to the window. The system rail is positioned at a distance from the window, which is not greater than about 20 c, preferably 10 cm. The system rail is thus suitably positioned for receiving at least one auxiliary device to be positioned at the window, such as a probe for determining relevant process parameters in the biological medium.

In an embodiment, the bioreactor system has at least one system rail near an upper edge of the receiving container, for attaching at least one auxiliary device. Thus also the individual attachment of auxiliary devices near the upper edge, i.e. near the stirring opening of the receiving container is provided. To this end, the system rail may be at least 10 cm long and/or be positioned in a substantially horizontal direction, approximately parallel to the upper edge of the receiving container.

A third aspect refers to a bioreactor system for receiving a disposable bag, having a receiving container for receiving the disposable bag and a cable guide on an outer wall of the receiving container, wherein the cable guide extends to a upper edge of the receiving container. The cable guide may also be a tube guide or a combined cable and tube guide.

The bioreactor system may be a bioreactor of above said kind. The bioreactor system of the third aspect is similar to the bioreactor system of the first and/or second aspect, so that most part or even the entire description of the bioreactor system of the first and/or second aspect may also be applied to the bioreactor system of the third aspect and vice versa.

In the bioreactor system of the third aspect, a cable guide is provided on an outer wall of the receiving container, which extends approximately up to the upper edge of the receiving container. The cable guide may essentially have a U-shape, wherein cable and/or tubes are inserted in the U-opening and are securely guided therein. The cable guide may additionally or alternatively be at least partially provided as a grid cable channel. The cable guide is generally adapted for securely receiving cables and/or tubes. Thus cables and/or tubes are secured and guided in a fixed nominal position on the receiving container, whereby the probability of an interaction between an operator and the cables and/or tubes is reduced, as well as the risk of an inadvertent detachment of a cable and/or tube and/or conduit. The cable guide extends to the upper edge of the receiving container and thus up to the stirring opening. Electric cables for a stirring motor and/or further supply lines for sensors have to be laid up to the stirring opening, for example, which enter into the stirring opening from above. Moreover, other auxiliary medium containers may be positioned at the stirring opening, through which medium may be fed into the receiving container. Herein, supply lines or tubes to the auxiliary medium containers may be guided through the cable guides.

The cable guide reduces the risk of tripping. The cable guide also reduces the risk of damaging the tubes and cables. Thus the operation of the bioreactor system is more user friendly.

The bioreactor system according to the third aspect may have all additional characteristics of the bioreactor system of the first and/or second aspect and vice versa.

According to an embodiment of the bioreactor with the cable guide, the cable guide has at least a partially meandering shape. In particular, the cable guide may have connector lids, which meanderingly engage a guide groove of the cable guide. The cable and/or the lines may thus be quickly and securely inserted or positioned behind the meandering connecting lids are guided thereat.

According to an embodiment of the bioreactor with the cable guide, the bioreactor system has a support bridge, which is disposed on the upper edge of the receiving container. The support bridge is positioned at least at a position on the upper edge of the receiving container, to which the cable guide leads. A stirring device and/or sensors of the bioreactor system may be positioned on the support bridge. The cable guide guides the cables and/or lines directly at least to an attachment point on the bridge, from which the cable or the lines are forwarded to the support bridge and to devices thereon. The bioreactor system preferably has two of such cable guides, which are essentially symmetrical to each other and which lead to the two attachment points of the support bridge on the upper edge of receiving container.

In an elaboration of this embodiment, the cable guide extends from the upper edge of the receiving container along its outer wall essentially vertically downwards to a swinging point, at which the cable guide extends away from the outer wall of the receiving container to an outer region of the bioreactor system. Thus, the cable guide is at least partially essentially vertical, i.e. up to and/or away from the upper edge of the receiving container, i.e. in an upper region of the bioreactor system. Thus, the cable guide is very compact at least in this upper region, and thus facilitates the operation or access to the stirring opening of the bioreactor system. The cable guide, starting from the upper edge, leads, at the earliest at the swinging point, away from the outer wall of receiving container, and thus in a region which is for example underneath the working platform and does almost not interfere with the access to the bioreactor.

In an elaboration of the embodiment with the cable guide, the latter is divided in two parts with at least a permanent cable guide and at least one additional cable guide. The division in a permanent and additional cable guide allows, on one hand, a fixed and secure guiding of the permanently laid cables and/or lines, on the other hand a comfortable and secure disposition of additional cables and/or lines, which are application specific and not always required.

According to an embodiment, the bioreactor system has an obscuration device for at least one observation window and/or an obscuration cover for obscuring an opening on an upper edge of the receiving container. In particular an obscuration device may be provided for each observation window in the receiving container, for example as rolling curtains, sliding curtains, an electro-chromic plate of electric obscuring material, etc. Due to the obscuration device, uniform reaction conditions are facilitated and in particular the risk of influencing the biological reaction by light is reduced. The same is true for an obscuration cover, which may be a pane applied over the stirring opening.

A fourth aspect refers to a method for receiving a disposable bag in a bioreactor system, having the following steps:
  providing a bioreactor system comprising a receiving container, wherein an outlet opening, which is tapered downwards relative to Earth's frame of reference, is formed in the bottom surface thereof;
  providing a disposable bag having a standardized drain port;
  attaching a drain port, which is complementary to the outlet opening, to the standardized drain port of the disposable bag;
  introducing the disposable bag into the receiving container of the bioreactor system, wherein the complementary drain port is arranged in the outlet opening.

The bioreactor system may in particular be configured as a bioreactor system according to the first aspect. The complementary drain port is a separate component, which is disposed on and/or around the standard drain port of the disposable bag.

In an elaboration, a tube is led through the outlet opening, wherein one end of the tube is attached to the complementary drain port. Herein, the complementary drain port is passed by means of the tube into the downwards tapering outlet opening, for example in that the tube is drawn downwards through the outlet opening together with the complementary drain port into the outlet opening.

By means of the method according to the fourth aspect, the alignment and introduction of any suitable disposable bag having any standardized drain port into the bioreactor system is simplified and improved.

The invention is described in more detail below with reference to embodiments which are shown in the figures. Individual features of the embodiments shown in the figures can be implemented in other embodiments. Some identical or similar features of the embodiments are denoted by the same reference numerals.

DETAILED DESCRIPTION

Figure 1:
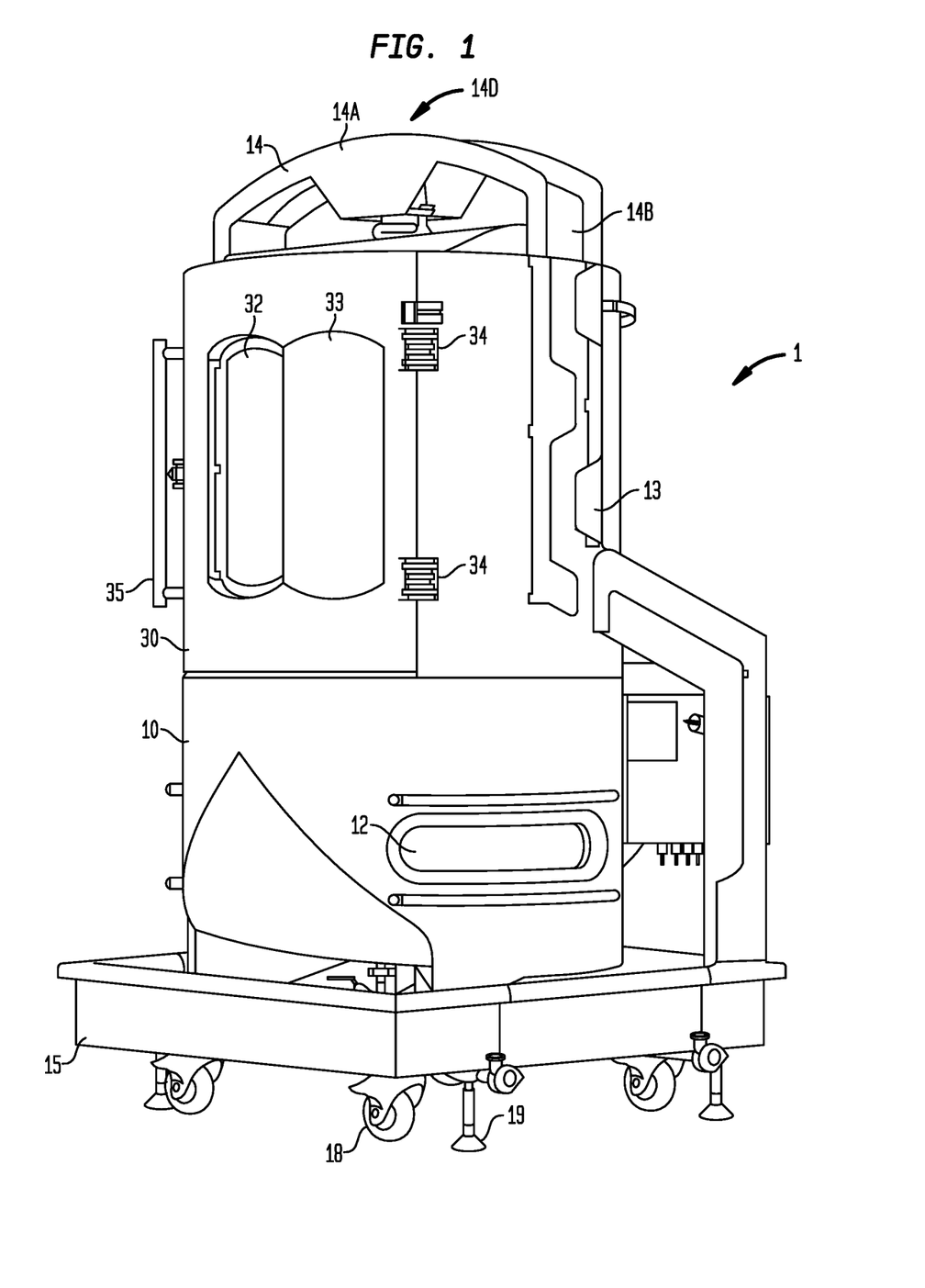
FIG. 1 shows a perspective view of a device for receiving a disposable bag.

FIG. 1 shows a perspective view of a device 1 for receiving a disposable bag. The device 1 shown in the figures can be formed as a part of a system and/or as a bioreactor system for receiving a disposable bag.

The device 1 comprises a receiving container 10, which essentially has the shape of a vertically arranged cylinder, i.e. whose cylinder axis is substantially vertically arranged. The receiving container 10 has a container inner space into which a disposable bag 44 (see FIG. 3) can be partially inserted at least partially, which, for example, may include a biological medium. The biological medium in the disposable bag 44 is stored in the inner space of the receiving container 10 over a specified (predetermined or predeterminable) period of time. While the disposable bag 44 is located with the biological medium in the interior of the receiving container 10, various reactions may occur with or in the biological medium. Thus, the device 1 may also be provided as a bioreactor and/or the bioreactor system.

In order to monitor the biological medium, one or more partially different observation windows 12, 32 are formed in the side wall or in the side walls, through which the interior of the receiving container 10 may be observed from outside through the container wall, in order to observe the biological medium. To this end, the device 1 has in the lower third two bottom windows 12, as well as a door observation window 32. The bottom windows 12 may be used for inserting at least one probe and/or at least one tube into the disposable bag, preferably have an essentially oblong oval form, whose long axis is essentially horizontally aligned along the curved cylindrical outer wall of the receiving container 10. The door observation window 32 is preferably shaped like an oblong rectangle, wherein its longer sides are essentially vertical. The door observation window 32 is preferably approximately centered in a single panel door 30 in the container wall of the receiving container 10.

Figure 2A:
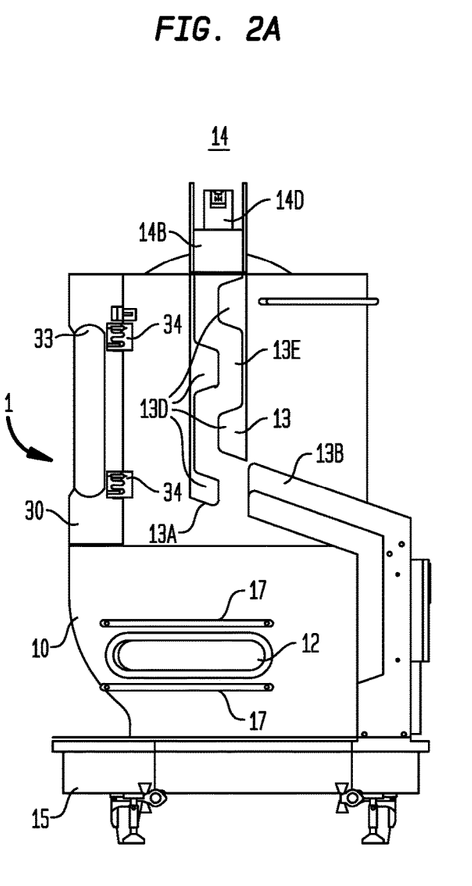
FIG. 2A shows a first side view of a device for receiving a disposable bag.
Figure 2B:
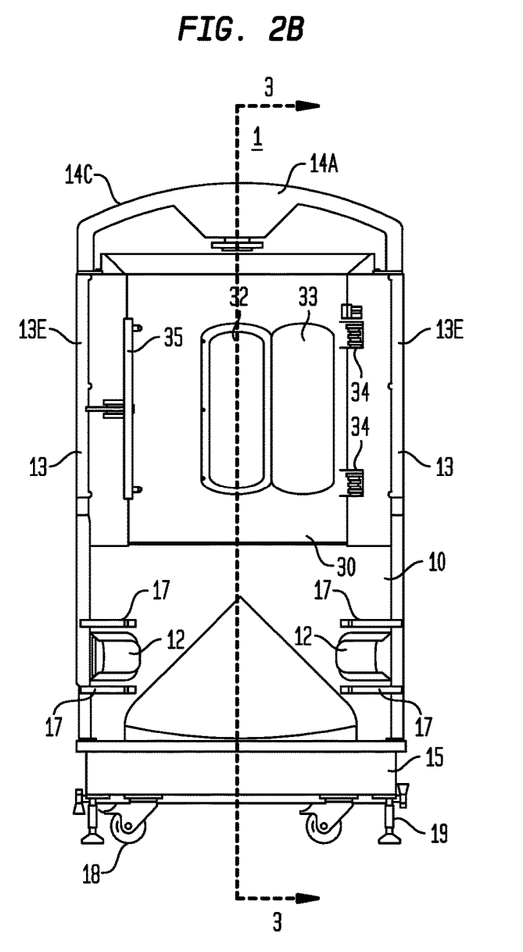
FIG. 2B shows a second side view of a device for receiving a disposable bag.

FIGS. 2A and 2B together with FIG. 1 show different views of device 1. For example, FIG. 2B shows a front side view of the one-paneled door 30. The one-paneled door 30 extends widthwise, thus in the horizontal direction, approximately over a segment of the side surface or cylinder of the receiving container 10 from about 70° to about 160° (for example about 100°). The one-paneled door 30 horizontally extends preferably from two door hinges 34 along the cylindrical side up to a door knob 35 at the opposed door end. The one-paneled door 30 is preferably and essentially formed in the upper half, in particular in the upper two thirds of the receiving container 10, while the lower half (preferably the lower third) of the receiving container 10 is essentially a rigid bottom shell, which cannot be opened. The one-paneled door 30 may be rotated or pivoted and thus opened about the door hinges 34. If the one-paneled door 30 is open, then in the receiving container 10 a door opening is formed laterally, through which access to the interior of receiving container 10 is allowed. For example, the disposable bag 44 may be preferably introduced from an essentially lateral or radial direction, thus essentially with a horizontal motion direction, in to the receiving container 10.

On the door observation window 32 an obscuration device as a door obscuration 33 is preferably disposed, which may be folded, slid, rolled or otherwise moved in front of the door observation window 32 in order to obscure the window 32. The door obscuration 33 obscures the inner space of container. A similar or different (bottom) obscuring may be preferably also provided for the bottom windows 12 and possibly for other observation windows.

The device 1 is mounted on rollers 18, by which the device may be pushed, by rolling or be displaced through a space. In addition to the rollers 18, the device 1 may have fixing feet 19 at the lower end which serve to fix and adjust the height of the device 1. The fixing feet 9 can also be used to compensate for an uneven ground.

Below the receiving container 10, a collecting tray 15 is arranged, which opens upwards and serves for at least partially collecting a biological medium and/or a thermal regulating medium which may possibly exit the container interior. The collecting tray 15 may preferably have a cladding made of plastic, which is adapted to the dimension of the collecting tray 15. Thus, the entire device 1 is protected, in particular any available weight cells and/or load cells. Moreover, the cladding improves biosafety, for example, by simple removal of contaminating biomaterial from the collecting tray 15 instead of subsequent cleaning thereof.

The collecting tray 15 is adjustable by an adjusting device. More specifically, the relative height of the collecting tray 15 can be adjusted by means of the adjusting device and/or the orientation below the receiving container.

Adjacent to the bottom windows 12 and/or to the door observation window 32 one or more system rails 17 may be disposed on the device 1, through which one or more auxiliary devices (such as probes and/or other mounts for special apparatus such as specimen removing systems, tubes or other mechanically relieving connections) maybe connected or secured to the disposable bag. In the device 1 one or more essentially horizontal system rails 17 are adjacent to the bottom windows 12, i.e. preferably each system rail 17 above and beneath each bottom window 12.

The receiving container 10 is essentially open at the top. Instead of a cylinder lid or independently thereof, the receiving container 10 has a stirring opening, which is preferably formed at or near the upper edge of receiving container 10. Above the open top of the receiving container 10 a stirring device 14 is formed or positioned, through which a stirring rod may be connected through the stirring opening to the disposable bag 44, so that the interior of the disposable bag 44 may be mixed. The stirring rod may be inside the disposable bag and may be connected through a joint or connection with the stirring device 14. The stirring device 14 is preferably centrally provided over the receiving container 10 and is supported by a support bridge 14A-C, which contacts or lies on an upper edge of the receiving container 10 on essentially opposed side walls of receiving container 10. The support bridge has one or more support elements 14C, which extend from at least one side wall of receiving container 10 at least partially over the upper opening thereof. In particular two support elements 14C are provided, which transversally extend over the receiving container 10 and lie or are supported by approximately opposite regions of the receiving container 10. Both support elements 14C are connected to each other by one or more (for example two) cross elements 14B. In a central region of the support bridge a stirring element receptacle 14A is provided, to which stirring elements of the stirring device may be attached, in order to mix or stir the content of the disposable bag 44 by means of the stirring rod through the stirring opening. A motor 14D is preferably secured to the stirring element receptacle 14A, for driving the stirring rod. Both support elements 14B and/or the stirring element receptacle 14A are shaped with flanks, for laterally protecting the motor 14D, so that the motor is protected from inadvertent collisions, for example, with external objects (a support crane, for example). Moreover, the stirring element receptacle 14A and/or one or more support elements 14C may have a support region 14E above the receiving container 10 or the disposable bag 44, on which one or more additional processing devices (such as filters, safety valve(s) and/or sensor(s)) may be disposed, through which the content of the disposable bag 44 may be processed and/or analyzed and/or kept or put into a specific (predetermined or predeterminable) state (such as temperature, pressure, $CO_2$ content, and/or $O_2$ content). In the attachment points of the support bridge on the container walls (in particular at the transition between the support element (2) 14C and lateral wall/s of receiving container 10) at least one cable guide 13 is formed or is attached.

FIG. 2A shows a side view of one of the two cable guides 13. The second of cable guides 13 is on the opposite outer wall of receiving container 10. The side view of FIG. 2A shows device 1 in a position rotated by 90° relative to side view of FIG. 2B.

The cable guide 13 has an upper cable guide 13E which is essentially directed vertically downwards from the upper edge of receiving container 10, i.e. at least up to half height of receiving container 10, at swing point 13A. The cable guide 13 extends from the swing point 13A further as a lower cable guide 13B laterally and/or rearwardly. The vertical part of cable guide 13 (i.e. the upper cable guide 13E) has one or more connecting lids 13D, behind which (or without which) cables and/or lines may be connected or positioned so that cables and/or lines may be guided and/or secured both from the outer wall of receiving container 10 inwardly and outwardly through the lid(s) 13D. The lids 13E engage, in a meanderingly way (or laterally alternating) in front of the upper cable guide 13E, so that the cable guide 13 is preferably at least partially formed in a meanderingly way.

The cable guide 13 may have formed components, into which one ore more cables and/or one or more tubes and/or one or more lines may be positioned or introduced. Moreover, the cable guide 13 may also have at least one pull safety. The cable guide 13 reduces the risk of inadvertent interaction with an operator (such as tripping) thus improving security and handling.

Figure 3:
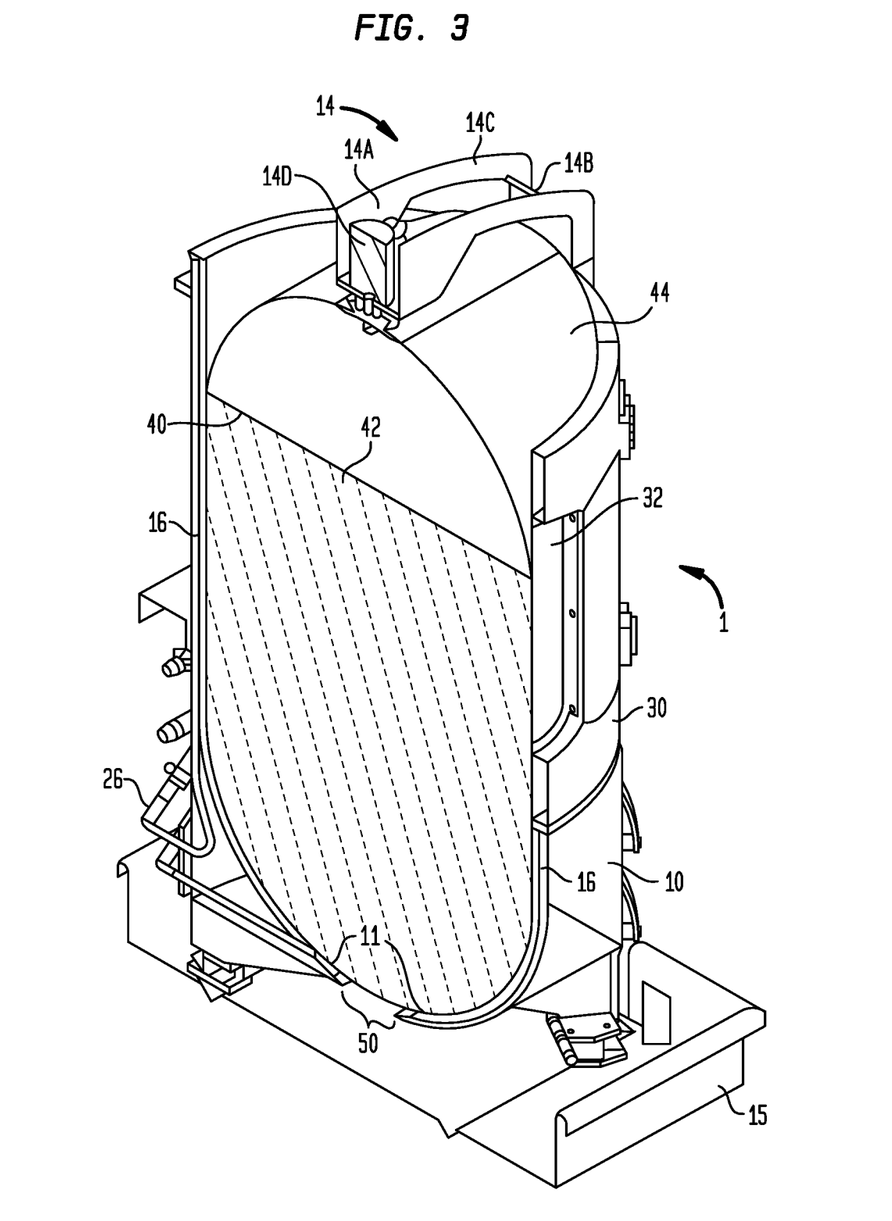
FIG. 3 shows a perspective representation of a vertical sectional view of a device for receiving a disposable bag.

FIG. 3 shows a perspective illustration of a view of a vertical section of device 1. FIG. 3 shows, for example, a disposable bag 44, more precisely a cross section through this disposable bag 44, which is arranged in the interior of the receiving container 10. In the receiving container 10 and at the same time in the interior of the disposable bag 44 is a biological medium 42 is arranged, which is filled up to the level of a predetermined filling level 40. The biological medium 42 extends from the bottom of the receiving container 10 up to a fill level 40 and thus fills preferably the entire internal volume of the receiving container 10 up to level 40, minus the volume of the walls of the disposable bag 44, which however are very thin and barely relevant.

The disposable bag 44 is supported and held substantially in shape by a container wall 16 of the receiving container 10, which preferably extends upwardly from a rounded bottom surface 11 of the receiving container 10 to above the liquid level 40. Thus, the bottom surface can be constructed for supporting the disposable bag 44. At least along the upper half, preferably along the upper two-thirds of the receiving container 10, the container wall 16 may substantially extend upwards in the vertical direction.

On the inner walls of the receiving container 10 a thermal regulating wall or thermal regulating hollow wall 20 is or may be disposed in the thermal regulating medium (not shown in the figures). The thermal medium is regulated preferably to a low pressure of less than 1 bar or less than 0.5 bar. The thermal regulating hollow wall 20 extends over the entire bottom of the receiving container 10 and along the container walls from the bottom surface 11 upwardly to beyond the filling level 40.

The biological medium 42 is (preferably in direct thermal contact) with the thermal regulating hollow wall 20 and may be put in thermal contact therewith, from which it is preferably only separated by the thin bag wall of the disposable bag 44. The biological medium can be controlled to a predeterminable temperature by the thermal regulating medium.

The device 1 may be particularly adapted and provided to control the temperature inside the container to a specific (predetermined or predeterminable) temperature.

The thermal regulating hollow wall 20 is at least partially surrounded on its outer side by a insulating hollow wall 25, in which preferably an insulation (for example PU foam or vacuum) is located. The insulating hollow wall 25 surrounds the interior of the receiving container 10 preferably almost completely from the bottom of the receiving container 10 up to the upper end of the container wall 16 (see. also FIG. 3). The insulating hollow wall 25 isolates both the container interior, and in particular the thermal regulating hollow wall 20 from the outside. By the insulation disposed in the insulating hollow wall a selective temperature regulation by means of the thermal regulating medium is provided towards the inside of the container interior, which increases the energy efficiency of the device 1.

The thermal regulating medium is preferably located within a closed temperature regulating system, which comprises the interior of the thermal regulating hollow wall 20. The regulation and/or control of the temperature of the thermal regulating medium may be provided via an internal, electrically-powered heating device and optionally or alternatively an external heat exchanger. Both a cooling and heating of the thermal medium can be performed by the external heat exchanger independently from the internal electric heater of the thermal regulating system.

The disposable bag 44 is emptied at least partially, for example after termination of the reaction through an outlet opening 5 disposed under the device 1 and may then be completely disposed of. A drain port 45 of the disposable bag 44 is supported or provided in the outlet opening 5, through which the disposable bag 44 may be emptied. The outlet opening 5 is formed in the bottom surface of the receiving container 10. By using the disposable bag 44 a cleaning of device 1 may be omitted, or may be accelerated.

Figure 4A:
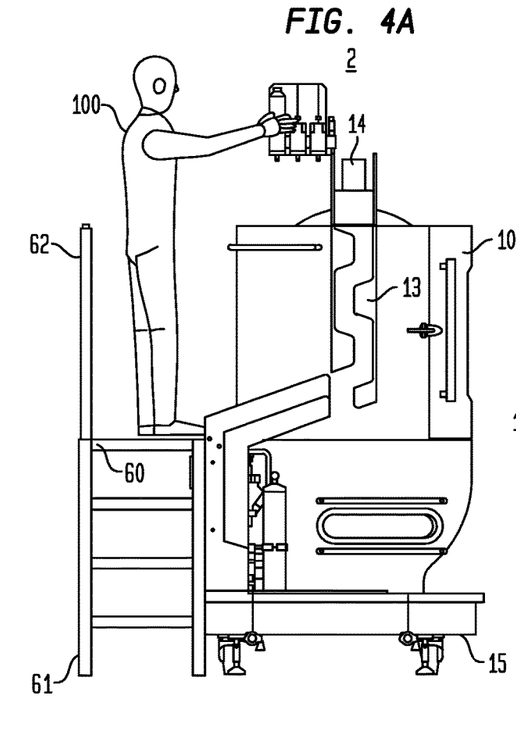
FIG. 4A shows a side view of a device for receiving a disposable bag having a high working platform.

FIG. 4A shows a side view of a device 2 for (at least partially) receiving a disposable bag with a (in particular high or heightened) working platform 60. The device 2 may in particular be provided as a bioreactor and/or bioreactor system for receiving a disposable bag.

On one side of bioreactor 2, the working platform 60 is formed, on which an operator 100 stands and operates the stirring device 14. Furthermore, the operator 100 has access, from the working platform 60, to one or more sensors which are formed on the stirring opening of the bioreactor 2.

The working platform 60 includes a walkable surface, on which the operator 100 shown in FIG. 4A is standing or can stand. This surface of working platform 60 is arranged as a high working platform and formed preferably at least at about 65 cm from the floor, for example at a height of about 118 cm. The accessible surface of the working platform is immediately adjacent to the receiving container 10 and preferably at least about 40 cm (for example, about 45 cm) wide. The walking surface extends from the receiving container 10 away (preferably over a width of about 45 cm) up to a platform end, which is opposite to the receiving container 10. On this platform end facing away of working platform 60 or the accessible surface of the working platform 60, a railing 62 is formed, which protects the operator 100 from falling down from the accessible surface.

Figure 4B:
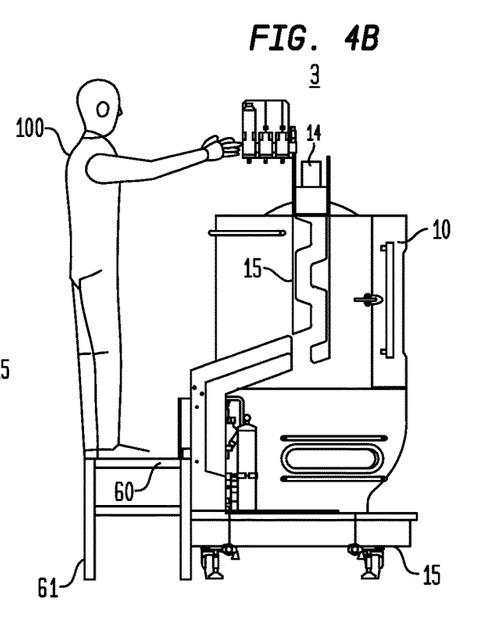
FIG. 4B shows a side view of a device for receiving a disposable bag with a low working platform.

FIG. 4B shows a side view of a device 3 for receiving a disposable bag with a (preferably low) working platform 60. The device 3 may be formed as a bioreactor and/or a bioreactor system for receiving a disposable bag.

The low working platform 60 of device 3 is similar to device 2 shown in FIG. 2. The low working platform 60 of device 3 is preferably disposed, however, only about 30 cm to about 64 cm above the ground and is preferably without a railing.

An obscuration device, not shown in figures, may obscure the upper stirring opening of the devices 1, 2 or 3. The obscuration is used (preferably along with the door obscuration and/or the two bottom window obscurations) for monitoring and/or controlling the incidence of light into the container interior.

Figure 5:
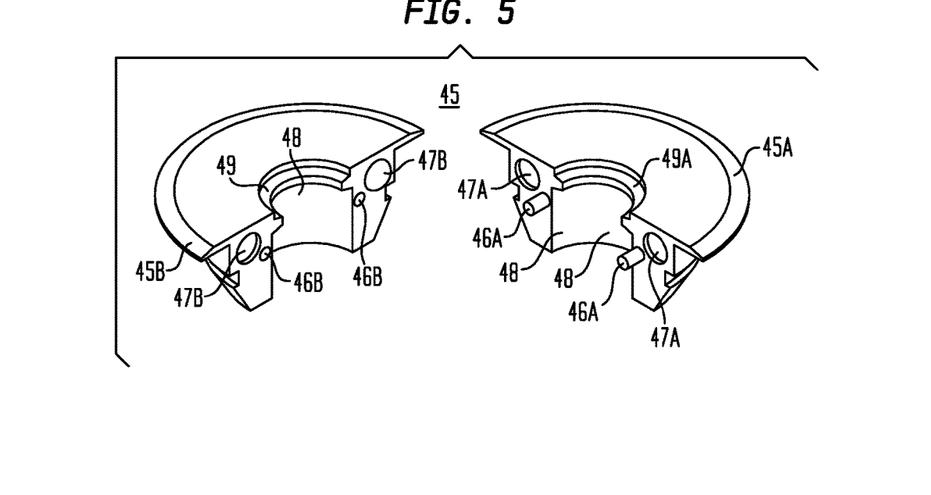
FIG. 5 shows a perspective view of a two-component conical drain port.

FIG. 5 shows a perspective view of a two-part conical drain port 45. The drain port 45 is adapted and provided to be attached to a standard drain port of a disposable bag 44, in order to provide the drain port of disposable bag 44 with a conical outer surface.

The drain port 45 is preferably designed as an independent component and can be formed as part of a bioreactor system, such as the device 1, 2 or 3. The drain port 45 is preferably formed in two parts and has a first partial shell 45A and a second partial shell 45B. The two partial shells 45A and 45B are substantially the same size and are adapted and provided for being assembled to form the composite drain port 45.

Each of the two partial shells 45A and 45B is preferably formed as a half-cone, with a tapered substantially conical outer surface and/or a substantially straight shaped sectional area inner side, in which a receptacle 48 is formed. The receptacle 48 is formed substantially in the form of a hollow cylinder and serves to receive a standardized drain port of a disposable bag. The sectional area of inner sides of the two partial shells or half-shells 45A and 45B are formed and provided, in order to be applied over each other on the entire surface. The (preferably substantially conical) drain port 45 is provided in this combination.

The first partial shell 45A has one or more (for example two) alignment pins 46A, which are formed on the inner side of the sectional surface and which protrude approximately vertically from the surface inner side. The one or more (for example two) alignment pins 46a are formed and provided for being at least partially inserted into one or more (for example two) complementary alignment openings 46B of the second partial shell 45B, thus aligning both partial shells correctly to each other. Additionally, on the inner sides of the section surface one or more magnets 47A and 47B are preferably disposed, which attract each other and/or draw and hold both shells 45A and 45B against each other. Both partial shells may be provided, in an alternative embodiment, with one or more hinges or joints, with which they may be folded onto each other in a target position.

The drain port 45 shown in FIG. 5 preferably has a preferably conical cylindrically symmetrical outer surface. Alternatively, the outer surface of the drain port may also have a hemispherical and/or semi-ellipsoidal shape. It is only important that in the outer form, the drain port in its composed form tapers in a direction (preferably with cylindrical symmetry), in particular in a direction away from the inner space of the disposable bag, in the operating position.

Figure 6A:
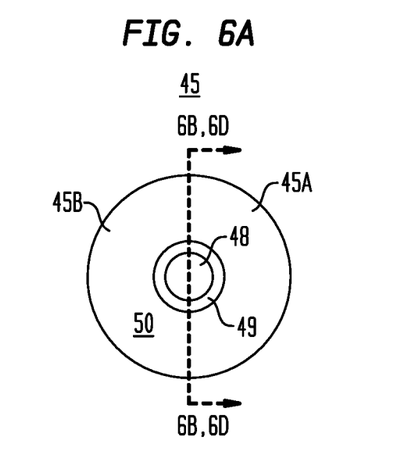
FIG. 6A shows a plan view of the two-component conical drain port of FIG. 5.

FIG. 6A shows a plan view of the conical drain port 45 in two parts of FIG. 5, in an assembled form. The centrally positioned receptacle 48 is clearly shown, in particular in the axial direction along the axis of the hollow cylinder forming the receptacle 48. In the plan view the drain port 45 essentially has a circular shape, wherein in the center the receptacle 48 is formed.

Figure 6B:
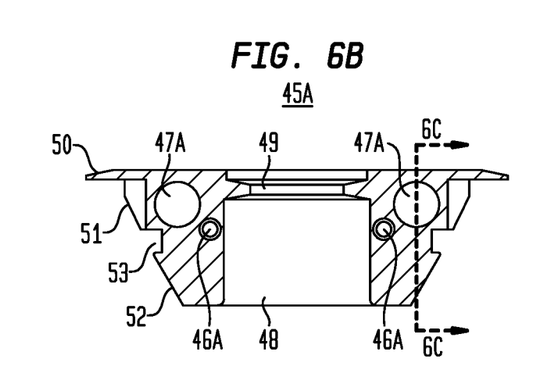
FIG. 6B is a cross sectional view of the two-component conical drain port taken along line 6B-6B of FIG. 6A.
Figure 6C:
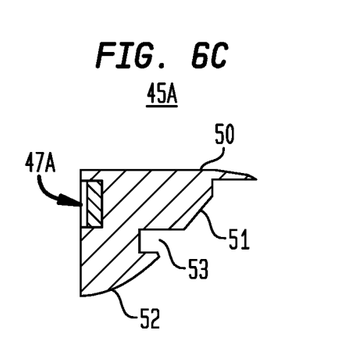
FIG. 6C is a cross sectional view of the two-component conical drain port taken along line 6C-6C in FIG. 6B.

FIGS. 6B and 6C show cross sections of the two-part conical drain port 45 of FIG. 5. On the left side of the cross section only the first partial shell 45A is shown, while on the right side a cross section of the second shell 45B is shown in particular perpendicularly to the plane of the inner side of section surface.

The drain port 45 is preferably essentially provided with a cylindrical symmetry with respect to a central axis, which coincides with the cylinder axis of receptacle 48. The drain port 45 has at the upper end a flange or a circular disc 50 shown in FIG. 6A. below the flange or circular disc 50, the outer surface of drain port 45 tapers along a first sliding surface 51 and a second sliding surface 52, between which a circular groove 53 is formed in the outer surface. The first sliding surface 51 is formed below the circular disc 50, the circular groove 53 is formed below the first sliding surface 51 and the second sliding surface 52 is below the groove 53. Alternatively, the groove 53 may be also disposed below a long sliding surface.

Figure 6D:
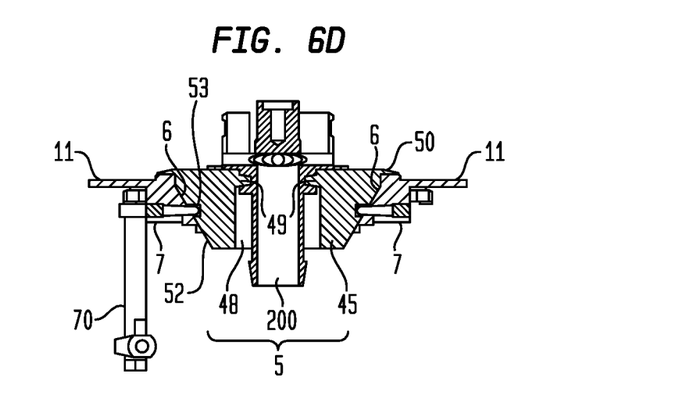
FIG. 6D is a cross-sectional view taken along line 6D-6D of FIG. 6A, but showing the two-component conical drain port in an operating position applied around a standardized drain port.

FIG. 6D shows a cross section of the two-part conical drain port 45 in an operating position, in which it is placed around a standard drain port 200. The drain port 45 is disposed with its two half-shells substantially around the standard drain port 200 of a commercially available disposable bag 44 and arranged so that the disposable bag 44 now has the cone-shaped drain port 45 as its drain connection, in particular exactly the downwardly tapering external dimensions.

Here, the standard drain port 200 is disposed in the hollow cylindrical receptacle 48, in such a way that the substantially cylindrical standard drain port 200 is held by means of a circular protrusion 49 in the receptacle 48. The circular projection 49 is formed as part of the drain port 45 in the receptacle 48, specifically at each of the two partial shells 45A and 45B. The circular projection 49 is directed approximately perpendicularly into the interior of the hollow cylinder, that is, perpendicularly to the cylindrical axis of symmetry of drain port 45, and provides engaging a corresponding recess in the standard drain port 200, as shown in FIG. 6D. The recess in the standard drain port 200 can be adapted in this case for a normal connecting of a tube or the like.

By the one or more magnets 47A and 47B and/or the one or more alignment pins in the alignment holes 46A 46B the two part shells 45A, 45B are firmly and stably maintained and positioned around the standard drain port 200 of the disposable bag. Alternatively or additionally, the part shells can also be arranged by means of a snap lock or other fixing means to the standard drain port 200 of the disposable bag. The disposable bag 44 thus provided with the drain port 45 can be introduced into one of the devices 1, 2 or 3, for example, as shown in FIGS. 1 to 4. In these devices, the receiving container 10 has a bottom surface 11 in which a downwards tapering outlet opening 5 is formed, as already shown in FIG. 3 and as an enlarged detail in FIG. 6C.

The outlet opening 5 is preferably formed with a substantially cylindrical symmetry about a vertical cylinder axis and has downwards tapering inner surfaces which are formed as support surfaces 6 for the outer surfaces of the draining port 45. The surfaces 6 are formed substantially complementary to the external dimensions of the drain port 45 and/or substantially adapted to the tapering of the first and second sliding surface 51 and 52. In particular, the slopes are matched to one another in cross section. In other words, the reduction of the internal radius along the symmetry axis of the outlet opening 5 downwardly is equal to the reduction of the outer radius along the axis of symmetry of the drain port 45 in the downward direction. The surfaces 6 thus have substantially the shape of a downwardly tapering cone.

During the introduction of the disposable bag 44 into the device 1, 2, 3 the drain port 45 slides or glides without much intervention by an operator, practically by itself, in the outlet port 5 in the bottom surface 11 of the receiving container. The drain port 45 can be guided to a tube or cord end into the receiving opening 5. Here, the drain port 45 slides together with the enclosed standardized drain port 200 so far into the outlet opening 5, that the flange and the circular disc 50 rests on the outlet opening 5. The circular disc 5 has an outer diameter which is larger than the inner diameter of the outlet opening 5. Therefore, the flange and the circular disc 50 as shown in FIG. 6C in the operating position lie flat on the bottom surface 11, centered on the axis of symmetry of the drain port 5. Except for the circular disc 11, the drain port 45 is disposed completely in the operative position in the outlet opening 5 and even passes through the same. Specifically, the first sliding surface 51 and the second sliding surface 52 lie flush on the surface 6. Further, the symmetry axis of the drain port 45 coincides, in the operating position shown in FIG. 6C, approximately with the axis of symmetry of the drain port 5.

In the outlet opening 5, at least one fixing element 7 is preferably arranged in the form of a bolt which at least partially engages in a closing position the circumferential groove 53 of the drain port 45, and fixes it in the outlet opening 5. The fixing element 7 is preferably movable perpendicularly to the central axis (i.e. the axis of symmetry) of the outlet opening 5 between a closed position and an open position. The fixing element 7 provides locking of the outlet opening 5.

In FIG. 6C the closing position of the lock, the fixing element 7, is shown, in which the drain port 45 is fixed by means of the fixing element 7 in the outlet opening 5 in the operating position.

The fixing element 7 can be opened and closed by means of a remote control 70. This remote control 70 is designed as a mechanical remote control, which is partially shown in FIG. 6C, but in more detail in FIGS. 7A-7C.

Figure 7A:
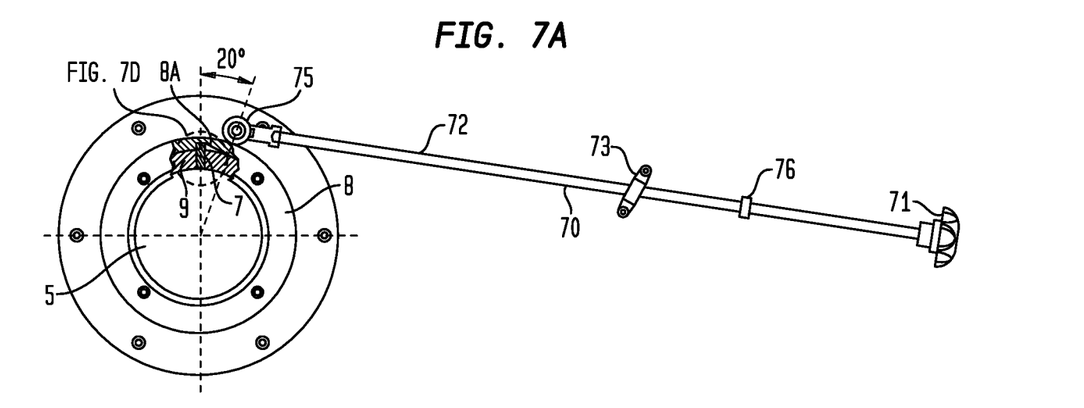
FIG. 7A shows a bottom view of a downwards tapering outlet opening with an open fixing element as well as corresponding mechanical remote control.

FIG. 7A shows a bottom view (that is, in a view from below in a vertical upward direction) of the downwardly tapering outlet opening 5 with an opened fixing element 7, and the associated mechanical remote control 70. The remote control 70 can be actuated by a handle 71 to which a horizontal bar 72 is attached, which is movable in an eyelet 73 up to a stop 76 in a substantially horizontal direction.

Figure 7B:
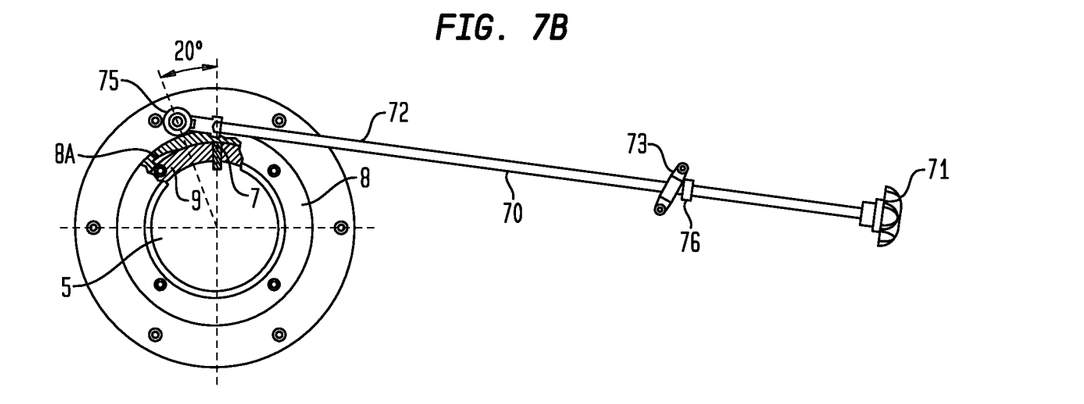
FIG. 7B shows a bottom view of a downwards tapering outlet opening with a closed fixing element and associated mechanical remote control.
Figure 7C:
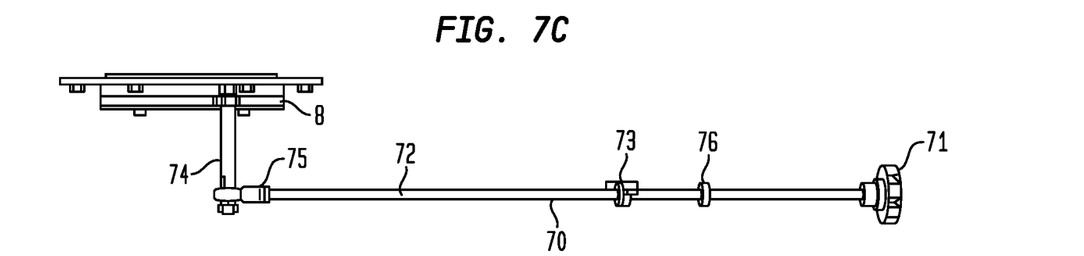
FIG. 7C shows a side view of a downwards tapering outlet opening with an associated mechanical remote control.
Figure 7D:
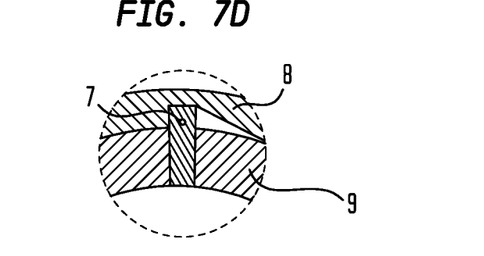
FIG. 7D is an enlarged view of the circled area of FIG. 7A.

FIG. 7C shows the remote control 70 in a side view. In the open position of FIGS. 7A and 7C of lock the handle 71 is at a maximum distance from the outlet opening 5. The handle 71 is disposed at one end of the horizontal bar 72, which is opposed from the outlet opening 5. An opposed end of the horizontal bar 72 is provided as a joint 75. In this joint 75 a vertical bar 74 is disposed which is fixed to a rotating ring 8.

The vertical bar 74 is preferably essentially vertically aligned and is thus approximately perpendicular to the horizontal bar 72 which is preferably essentially horizontal. The vertical bar 74 may be shorter than the horizontal bar 72. In an alternative embodiment, the vertical bar 74 may be omitted, in particular with differently accessible bioreactor systems.

The rotating ring 8 is supported in a rotatable way about the outlet opening 5, more precisely about a fixing ring 9 (see FIG. 7A). the rotating ring 8 may be rotated about a vertical central axis (thus the symmetry axis) of outlet opening 5, in particular between the closed and open position. The latter is shown in FIGS. 7A and 7C. The fixing ring 9 is at least partially disposed around the outlet opening 5, is stationary and is used an inner rotating anchor, about which the outer rotating ring 8 is rotatably supported.

Alternatively, or additionally to the rotating ring, the device may have a cursor, with which the drain port 45 may be locked in or on the outlet opening 5.

In the open position, the rotating ring 8 is aligned with respect to the fixing ring 9 so that a cavity 8A in the inner surface of the rotating ring 8 is exactly at the height of the fixing element 7. The fixing element 7 has a spring, which radially outwardly biases the fixing element 7 from the central axis of the outlet opening 5, in particular in the open position, into the cavity 8A in the rotating ring 8. Thus outwardly pressed, the fixing element 7 does not protrude anymore inside the outlet opening 5, being instead essentially flush with the surfaces 6 of outlet opening 5 and thus essentially frees the entire outlet opening 5.

The exact position of the rotating ring 8 relative to fixing ring 9 and in particular the engagement of the fixing element 7 into the cavity 8A is also shown in FIG. 7A in an enlarged view. In the open position, the conical drain port 45 of a disposable bag may freely slide into the outlet opening.

The closed position, in which the fixing element 7 protrudes towards the central axis into the outlet opening 5, is shown in FIG. 7B. In order to pass from the open into the closed position, the handle 71 of remote 70 is moved in the direction of the outlet opening. The horizontal bar 72 is moved through the stationary eyelet 73, until the abutment 76 abuts against the eyelet 73. The abutment 76 is larger than the eyelet opening of eyelet 73.

During this closing movement, the joint 75 and thus also the vertical bar 74 are moved towards the handle 71. The rotating ring 8 rotates about the fixing ring 9. The cavity 8A is moved relative to element 7, i.e. away from it. In the closed position, the rotating ring 8 lies with its inner side directly on the outer sides of fixing ring 8 and presses or engages the fixing element 7 inside the outlet opening 5. In the closed position, the cavity 8A is thus preferably offset with respect to fixing element 7.

The rotation of the ring 8 from the open position to the closed position can be carried out over a rotational angle of about 20° to about 60°, in the example embodiment shown in the figures, over a rotation angle of approximately 40°.

When the handle 71 again moves away from the drain port 5, the rotating ring 8 rotates back until the recess 8A is again arranged at the height of the fixing element 7, which springs back in the recess 8A and blocks the further rotational movement. The fixing element 7 thus also serves as a limit of the opening movement while the abutment 43 formed about the horizontal bar 72 limits the closing movement.

The remote control 70 facilitates fixing the drain port 45 in the outlet opening 5 on the bottom surface 11 of the receiving container 10 which is difficult to reach.

Instead of the drain port 45, which is placed as a separate component around a standard drain port, a disposable bag can be used with an already built-in (preferably conical) drain port for introduction into the bioreactor system.

In an alternative embodiment (not shown) the drain port may also consist of more than just two components be constructed and/or be provided instead of (or in addition) to the magnets with mechanical fixing devices such as locking hooks etc.

The locking mechanism of the outlet opening can not only be used for locking the drain port, but also for fixing of any other port of the disposable bag in another bag position.

Alternatively to the illustrated locking with the rotating ring, the drain port may also be fixed by a sliding mechanism engaging in the circumferential groove.

Figure 8A:
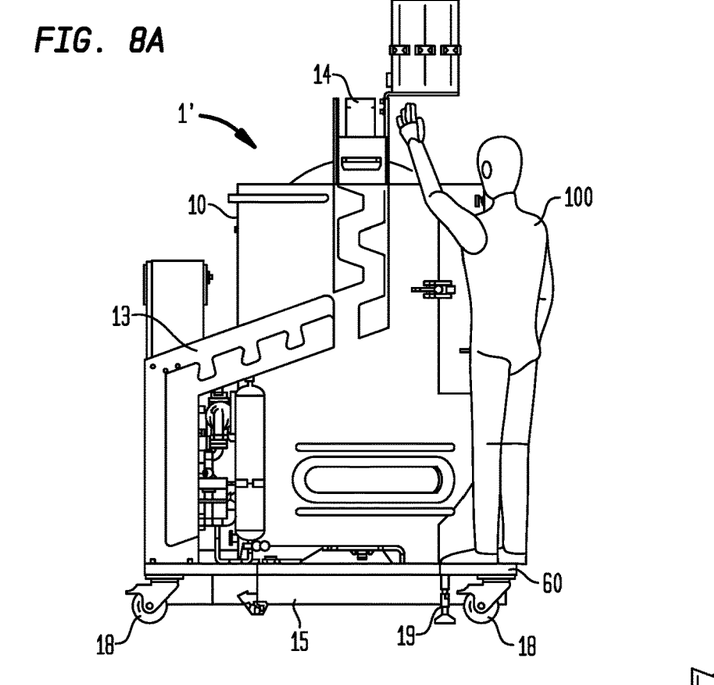
FIG. 8A shows a side view of a device for receiving a disposable bag having a working platform.
Figure 8B:
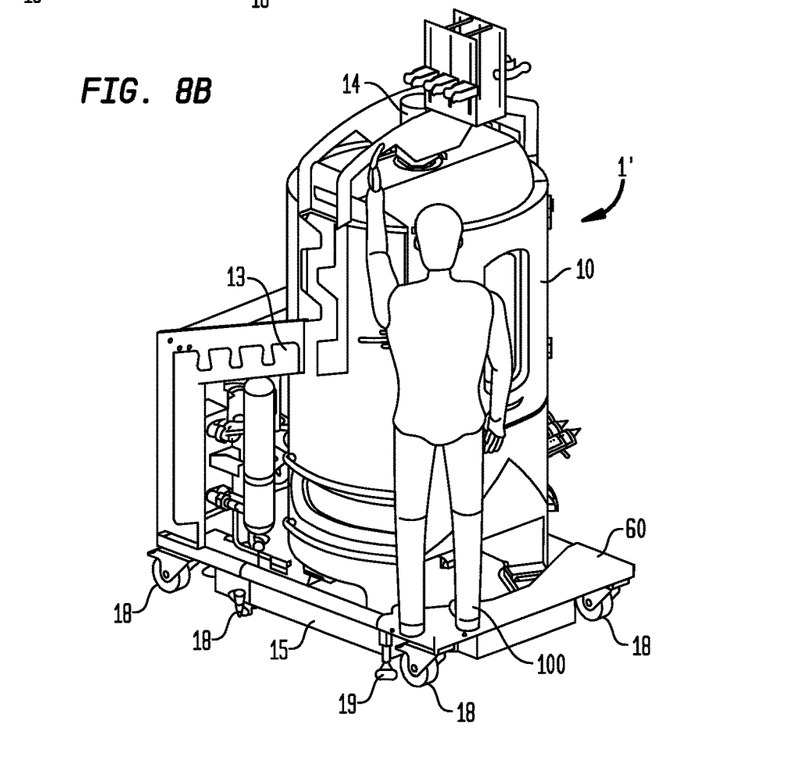
FIG. 8B shows a perspective view of a device for receiving a disposable bag with a working platform.

FIGS. 8A and 8B show a side view and a perspective view of a device 1' for (at least partially) receiving a disposable bag with a working platform 60. The device 1' can in particular be formed as a bioreactor and/or a bioreactor system for receiving a disposable bag.

On one side of bioreactor 1', the working platform 60 is formed, on which an operator 100 stands and operates the stirring device 14. Furthermore, the operator 100 has access, from the working platform 60, to one or more sensors which are formed on the stirring opening of the bioreactor 1'.

The working platform 60 includes a walkable surface, on which the operator 100 shown in FIGS. 8A and 8B is standing or can stand. This surface of the working platform 60 is disposed and formed as a working platform.

The walkable surface of the working platform is adjacent to the receiving container 10 and preferably is at least about 40 cm wide at least at one corner of the device 1'. The walkable surface extends from the receiving container 10 away to a platform end opposite with respect to the receiving container 10.

The working platform 60 is formed as a tread surface that the operator 100 can enter to more easily reach the stirring device 14 and/or the associated motor. In the embodiment shown, the working platform is formed as a walkable surface 60, for example, which rests directly on the collecting tray 15 and/or is fastened to the collecting tray 15, and in particular at or on an upper edge of the collecting tray 15. Thereby, the working platform 60 can be implemented in a particularly uncomplicated, cost- and/or space-saving way.

The collecting tray 15 is in this case designed such that the receiving container 10 is in the collecting tray 15. Further, the rollers 18 and/or the fixing feet 19 of the device 1' are formed so that they are recessed and/or integrated into the collecting tray 15. The collecting tray 15 is "at a lower position" compared to the embodiments shown in FIGS. 4A and 4B, whereby the total height of the device 1' can be reduced. This can be achieved in that the rollers 18 and/or the feet 19 are at least partially attached to an upper edge of the collecting tray 15 and/or are secured to this upper edge, and therefore either do not need or only need a reduced space below the collecting tray 15.

For example, four of the rollers 18 may be disposed at corners of the collecting tray 15, projecting laterally from the receiving container 10 and therefore need not have a collection volume. At these positions, the collecting tray 15 may be sufficiently spaced from the bottom, thus providing a sufficient free space for the rollers 8.

Below the receiving container 10, the collecting tray 15 may have a collecting volume which extends to near the ground. In other words, the collecting tray can be positioned up to about 5 cm from the ground, below the receiving container 10, preferably not more than about 3 cm, particularly preferably at a maximum distance of about 1 cm.

Herein, the height of the device 1' can be reduced while improving the accessibility of the stirring device 14 and/or of the associated motor by the operator 100.

The construction of the working platform 60 as a relatively low tread board over the lower positioned collecting tray 15 also allows the omission of a railing 62 of the working platform 60, such as in the case of the high working platform 60 in FIG. 4A. Thus the complexity of the components in manufacturing the device 1' is reduced.

LIST OF REFERENCE NUMBERS 1 device
1' device
2 device
3 device
5 outlet opening
6 support surface
7 fixing element
8 rotating ring
8A cavity
9 fixing ring
10 receiving container
11 bottom surface
12 bottom window
13 cable guide
13A swing point
13B lower cable guide
13D connecting lids
13E upper cable guide
14 stirring device 14A receptacle for stirring element
14B transversal element
14C support element
14D motor
14E support region
15 collecting tray
16 container wall
17 system rail
18 rollers
19 fixing feet
20 temperature regulating hollow wall
25 insulating hollow wall
30 one-paneled door
32 door observation window
33 door obscuration
34 door hinge
35 door knob
40 filling level height
42 biological medium
44 disposable bag
45 drain port
45A first partial shell
45B second partial shell
46A alignment pin
46B alignment opening
47A magnet
47B magnet
48 receptacle
49 circular protrusion
50 circular disc
51 first sliding surface
52 second sliding surface
53 circular groove
60 working platform
61 ladder
62 railing
70 remote control
71 handle
72 horizontal bar
73 eyelet
74 vertical bar
75 joint
76 abutment
100 operator
200 standardized drain port

What is claimed is:

1. A bioreactor system (1; 2; 3) for receiving a disposable bag (44) comprising
a receiving container (10) for receiving the disposable bag (44);
a working platform (60) which is arranged essentially adjacent to an outer wall of the receiving container (10); and
a collecting tray (15) arranged below the receiving container (10) for collecting a fluid exiting the receiving container (10), wherein:
a surface of the working platform (60), on which an operator (100) can walk, is arranged approximately 80 cm to about 140 cm below an upper edge of the receiving container (10);
the surface of the working platform (60) is arranged at a maximum height of about 65 cm above the ground and the working platform is not provided with a railing; and
the working platform (60) is formed as a tread surface resting on the collecting tray (15) and/or being fastened to the collecting tray (15).

2. The bioreactor system of claim 1, comprising an integrated ladder (61), which leads from the ground, on which the bioreactor system (1; 2; 3) is resting, to the walkable surface of the working platform (60).

3. The bioreactor system of claim 1, wherein the working platform (60) is configured to be at least partially extracted and/or swung open.

4. The bioreactor system of claim 1, wherein the collecting tray (15) has a plastic cladding and/or its position underneath the receiving container (10) is configured to be exactly adjusted.

5. The bioreactor system of claim 1, further comprising a system rail (17) for mounting at least one auxiliary device.

6. The bioreactor system of claim 5, wherein the system rail (17) is provided at a distance of about 3 cm to about 20 cm from an observation window (12, 32).

7. The bioreactor system of claim 1, further comprising a system rail arranged near the upper edge of the receiving container (10), for mounting at least one auxiliary device.

8. The bioreactor system (1; 2; 3) of claim 1, further comprising
a cable guide (13) on an outer wall of the receiving container (10), wherein the cable guide (13) is formed up to an upper edge of the receiving container (10).

9. The bioreactor system of claim 8, wherein the cable guide (13) is at least partially formed in a meander shape.

10. The bioreactor system of claim 8, comprising a support bridge, which is arranged on the upper edge of the receiving container (10), wherein the support bridge is arranged at least at one point on the upper edge of the receiving container (10), to which the cable guide (13) is leading.

11. The bioreactor system of claim 8, wherein the cable guide (13) extends from the upper edge of the receiving container (10) along its outer wall essentially vertically downwards to a swing point (13A), at which the cable guide (13) extends away from the outer wall of receiving container (10) and towards an outer region of the bioreactor system (1; 2; 3).

12. The bioreactor system of claim 8, wherein the cable guide (13) is formed in two parts with at least one permanent cable guide and at least an auxiliary cable guide.

13. The bioreactor system of claim 1, comprising an obscuration device (33) for at least one observation window (32) and/or an obscuration lid for obscuring an opening on an upper edge of the receiving container (10).

* * * * *